(12) United States Patent
Young et al.

(10) Patent No.: US 8,143,456 B2
(45) Date of Patent: Mar. 27, 2012

(54) METHOD OF REDUCING METHANOL IN RECYCLE STREAMS IN BISPHENOL-A PRODUCTION PROCESS

(75) Inventors: Thomas C. Young, Brazoria, TX (US); Michael D. Cloeter, Lake Jackson, TX (US); Mark E. Busbice, Brazoria, TX (US)

(73) Assignee: Dow Global Technologies LLC, Midland, MI (US)

( * ) Notice: Subject to any disclaimer, the term of this patent is extended or adjusted under 35 U.S.C. 154(b) by 109 days.

(21) Appl. No.: 12/671,705

(22) PCT Filed: Aug. 22, 2008

(86) PCT No.: PCT/US2008/073958
§ 371 (c)(1),
(2), (4) Date: Feb. 2, 2010

(87) PCT Pub. No.: WO2009/032552
PCT Pub. Date: Mar. 12, 2009

(65) Prior Publication Data
US 2011/0137087 A1    Jun. 9, 2011

Related U.S. Application Data

(60) Provisional application No. 60/968,766, filed on Aug. 29, 2007, provisional application No. 60/984,199, filed on Oct. 31, 2007.

(51) Int. Cl.
*C07C 37/20*    (2006.01)

(52) U.S. Cl. .................................................. 568/728
(58) Field of Classification Search ................ 568/728
See application file for complete search history.

(56) References Cited

U.S. PATENT DOCUMENTS

| | | |
|---|---|---|
| 5,777,180 A | 7/1998 | June et al. |
| 6,740,784 B2 | 5/2004 | Iwahara et al. |
| 6,943,273 B2 | 9/2005 | Saruwatari et al. |
| 7,129,382 B2 | 10/2006 | Iwahara et al. |

FOREIGN PATENT DOCUMENTS

| | | |
|---|---|---|
| EP | 0567857 | 11/1993 |
| EP | 1683779 | 7/2006 |
| JP | 9278703 | 10/1997 |
| JP | 6092889 | 12/2003 |
| WO | 9722573 | 6/1997 |
| WO | 02085830 | 10/2002 |
| WO | 2007086239 | 8/2007 |

OTHER PUBLICATIONS

International Search Report & Written Opinion from related PCT application PCT/US2008/073958, dated May 13, 2009, 9 pages.
International Preliminary Report on Patentability from related PCT application PCT/US2008/073958, dated Dec. 15, 2009, 8 pages.

*Primary Examiner* — Sikarl Witherspoon
(74) *Attorney, Agent, or Firm* — Brooks, Cameron & Huebsch, PLLC

(57) ABSTRACT

Methods for removing methanol from acetone recycle streams during bisphenol-A production, thereby avoiding the deactivation of catalyst, by distilling an acetone-methanol-water comprising mixture such that acetone is taken overhead in form of a relatively pure distillate, and substantial portions of the methanol and the water are leaving with the bottom product.

16 Claims, 1 Drawing Sheet

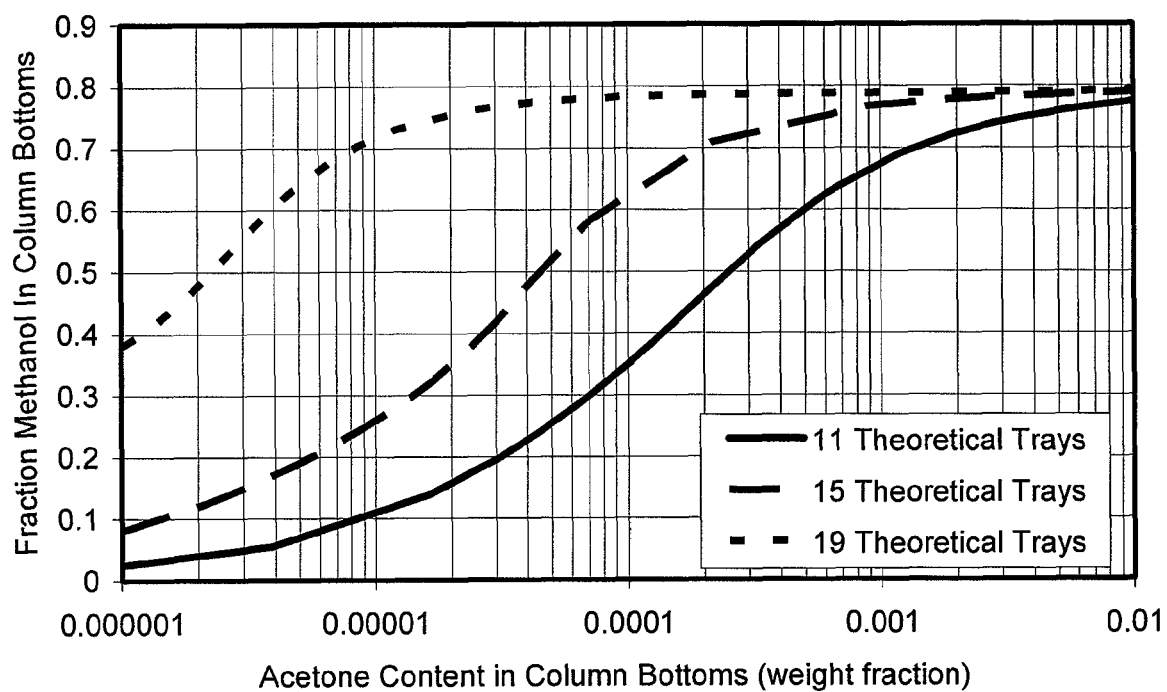

METHOD OF REDUCING METHANOL IN RECYCLE STREAMS IN BISPHENOL-A PRODUCTION PROCESS

CROSS REFERENCE TO RELATED APPLICATIONS

This is a §371 application of PCT International Patent Application Number PCT/US 2008/073958 filed Aug. 22, 2008, and claims priority from provisional application Ser. No. 60/968,766 filed Aug. 29, 2007, each of which is incorporated herein by reference in its entirety.

FIELD OF THE INVENTION

The present invention relates to a method of separating methanol from acetone recycle streams during the production of bisphenol-A, thereby avoiding the deactivation of mercaptoamine-promoted bisphenol-A catalysts.

BACKGROUND OF THE INVENTION

Bisphenol-A production is commonly done by reacting phenol and acetone using strong acid sulfonated styrene/divinylbenzene ion exchange resin catalysts, which are partially neutralized with mercaptoamine promoters. Methanol and other aliphatic alcohols are typically present in small amounts in the acetone raw material, and are believed to deactivate mercaptoamine-promoted bisphenol-A catalysts.

In a bisphenol-A production process, distillation is typically used to remove acetone and water from either the reactor effluent or the mother liquor from a phenol/bisphenol adduct crystallization step. This distillation step also removes methanol and other alcohols with the acetone and water, and some phenol and bisphenol may also be codistilled. This first distillation step is commonly referred to as the "drying column" or "lights removal column." A second distillation step is also typically used to recover acetone from the aqueous acetone mixture from the first distillation step. This second distillation step is commonly referred to as the "acetone recovery column." Typically, the methanol is also codistilled with the acetone, and the recovered methanol-containing acetone is recycled to the reactor for reuse. Since methanol does not readily react in a bisphenol-A process, this recycling can result in the accumulation of methanol in the process, which accelerates the deactivation of the catalyst. It would, therefore, be desirable to remove methanol from the bisphenol-A process to prevent deactivation of the catalyst.

EP 1 683 779 A1 discloses a process for producing bisphenol A wherein said process inhibits deterioration of the cation exchange resin catalyst used in the reaction step to prolong the catalyst life by reducing the lower alcohols such as methanol contained as impurities in acetone which is used as one of the raw materials. WO 2007/086239 A1 also discloses a bisphenol A production method which prevents a decline in bisphenol A production catalyst activity in the bisphenol A production method step in which the impurities present in a portion of the mother liquor obtained in a bisphenol A separation step are treated and the mother liquor is subsequently re-supplied to the reaction system. Neither of the above two references disclose a method of separating methanol from acetone recycle streams during production of bisphenol-A in a single acetone recovery distillation column, wherein a substantial amount of methanol leaves with the bottoms product form the bottom section of the distillation column.

Distillative separation of methanol from acetone is known to be difficult, due to the formation of azeotropes. Several alternatives for separating methanol from acetone have been proposed, including adsorption, reaction of methanol with another chemical followed by distillation, and extractive distillation using another extractive agent. However, each of these potential solutions would likely require additional equipment and/or the introduction of additional chemicals to the process. Further, these solutions would be expensive to implement. Thus, there is a continuing need for a low-cost and easy-to-implement solution for removing methanol from a bisphenol-A production process.

SUMMARY OF THE INVENTION

The present invention provides methods of removing methanol from acetone recycle streams during production of bisphenol-A, comprising: (a) introducing the condensed overheads from the bisphenol-A process drying column as a feed at a feed point into a distillation column comprising a reboiler and a condenser; (b) condensing a vapor from a top section of the distillation column and returning at least a portion of the condensed vapor to the column as a reflux; and (c) adjusting a flow rate of the feed, a flow rate of the reflux and a flow rate of the steam fed to the reboiler such that at least 20% of the methanol is leaving with a bottom product of a bottom section.

In one aspect of the method, the distillation column comprises at least 6 or more trays, such as 10, 12, 13, 15, 17, 19, 25, 35, 50, 100, or more trays, or packing equivalent to that number of trays. In another aspect, the distillation is preferably operated at a pressure ranging from about 0.5 to about 2.0 atmospheres. In a more preferred aspect, the distillation is operated at about atmospheric pressure. In yet a further aspect of the method, the reflux is set to be a fixed flow rate or a flow rate calculated to be a fixed multiple of the feed flow rate. In a still further aspect of the method, at least 20%, for example as 30, 40, 45, 50, 55, 60, 65, 70, 75, 80, 85, 90, or even 95% of the methanol is leaving with the bottom product.

In another aspect of the method, the distillation column comprises a thermocouple in the bottom section of the column, which acts as a control thermocouple. For example, the temperature may be controlled in the bottom section of the distillation column to cause at least about 20% of the methanol to leave with the bottoms product, while maintaining a bottoms acetone concentration of less than 10,000 ppm. More preferably, the bottoms acetone concentration is 1000 ppm or lower. Most preferably, the bottoms acetone concentration is 100 ppm or lower. In yet another aspect of the method, additional water as an extraction agent may be added, whereby the water is added preferably above the feed point.

The present invention also provides a process for the manufacture of bisphenol-A, comprising: (a) reacting phenol and acetone in the presence of a thiol-modified strong acid cation exchange resin catalyst to produce a reactor effluent containing bisphenol-A; (b) distilling the reactor effluent to remove water, methanol and unreacted acetone; (c) further distilling the water and acetone-rich overheads stream from the first distillation step to recover the unreacted acetone from the water, characterized in that at least 20% of the methanol fed to the second distillation step is leaving with the water stream; and (d) returning at least a portion of the overheads stream from the second distillation step (step (c) above) to the reactor as recovered acetone.

In another aspect of the process, the reactor effluent is: (e) subjected to a crystallization step to precipitate bisphenol/phenol adduct crystals; and (f) the solid/liquid mixture from the crystallization step is then subjected to a solid/liquid separation step to remove the adduct crystals before the crystal-free liquid from the solid/liquid separation step is distilled as described in step (b) in the preceding paragraph.

The present invention provides at least the following advantages and features: It is a low-cost and easy to implement solution for removing methanol from a bisphenol-A production process, thereby avoiding the deactivation of catalyst. The method allows the use of any distillation column, including those normally used for acetone recovery, in a bisphenol-A process.

Other features and advantages of the present invention will be set forth in the description of invention that follows, and will be apparent, in part, from the description or may be learned by practice of the invention. The present invention will be realized and attained by the methods and devices particularly pointed out in the written description and claims hereof.

BRIEF DESCRIPTION OF THE DRAWINGS

The above-mentioned and other features and advantages of this invention, and the manner of attaining them, will become more apparent and the present invention will be better understood by reference to the following description of an embodiment of the present invention taken in conjunction with the accompanying drawing, wherein:

The sole FIGURE is FIG. 1 showing a graph of the predicted performance of an atmospheric distillation column for methanol removal.

DETAILED DESCRIPTION OF THE INVENTION

The particulars herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those skilled in the art how the several forms of the present invention may be embodied in practice.

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being approximations. Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from 1 to 50, it is deemed to include, for example, 1, 7, 34, 46.1, 23.7, or any other value or range within the range.

The present invention provides a low cost and easy to implement method which separates methanol from acetone recycle streams during the production of bisphenol-A. The methanol separation is performed by way of distillation, whereby an acetone-methanol-water mixture is controlled in such a way that acetone as the solvent with the greatest volatility is taken overhead in form of a relatively pure distillate, and methanol and water leave via the column bottom. The acetone recycle stream may be derived from the reactor effluent or the mother liquor from a phenol/bisphenol adduct crystallization step. In a bisphenol-A production process, distillation is typically used to remove unreacted acetone and water from either the reactor effluent or the mother liquor from a phenol/bisphenol adduct crystallization step. This distillation step also removes methanol and other alcohols with the acetone and water, and some phenol and bisphenol may also be codistilled. This first distillation step is commonly referred to as the "drying column" or the "lights removal column." The overheads from this distillation step comprises acetone, water, phenol, bisphenol, and methanol.

The method of the present invention comprises introducing the overheads from the drying column as a feed at a feed point into a distillation column, having a reboiler and a condenser. This second distillation step is commonly referred to as the "acetone recovery column." The reboiler and condenser may be set to control the flow rate of the feed, the flow rate of the reflux and the heat input into the reboiler such that at least 20% of the methanol entering the column will leave with the bottom product and highly purified acetone will be taken from the column top. In some embodiments, at least 40%, such as 45, 50, 55, 60, 65, 70, 75, 80, 85, 90, or even 95% of the methanol is leaving with the bottom product. Optionally, additional water may be added, preferably above the feed point of the column, to enhance the separation of the methanol from the acetone.

The distillation column used in the method of the present invention may be any distillation column that is currently applied for acetone recovery in a bisphenol-A process. The distillation column may comprise at least 6 trays or packing equivalent to at least 6 trays. Non-limiting examples of the amount of theoretical trays include, e.g., 8, 10, 11, 12, 13, 15, 17, 19, 25, 35, 50 trays, or even 100 or more trays. Preferably, the distillation column may comprise from 10 to 50 trays, or packing equivalent to 10 to 50 trays. Preferably, the distillation column trays or packing are arranged in two sections, with one section of trays or packing above the feed point and one section of trays
below the feed point. Preferably, a distillation column containing packing will also contain distributors to ensure even distribution of the liquid feed and the reflux across the packing.

The distillation column may be operated at a pressure in the range of 0.5 atmospheres (51 kPa) to 2.0 atmospheres (203 kPa). Preferably, the distillation column may be operated at about atmospheric pressure.

The method of the present invention may be performed in such a way that a substantial portion of the methanol in the feed is leaving with the bottom product, while most of the acetone entering the column is recovered as purified acetone. Preferably, at least 20% of the methanol entering the column is leaving with the bottom product. Most preferably, the distillation column may be operated such that 30%, or 40%, or more of the methanol entering the column is separated.

Furthermore, according to the present invention, the distillation column may be regulated such that the leaving bottom product comprises an acetone concentration of less than 10,000 ppm; preferably, the leaving bottom product comprises an acetone concentration of less than 1,000 ppm; most preferably, the leaving bottom product comprises an acetone concentration of less than 100 ppm.

The present invention also provides a method of separating methanol from acetone recycle streams during production of bisphenol-A, comprising: (a) introducing an overhead product from a drying column or a lights removal column in a bisphenol process as a feed at a feed point into a distillation column comprising a reboiler and a condenser; (b) introducing water as an extraction agent into the column; and (c) setting a flow rate of the feed that at least 20% of the methanol leaves with a bottom product of a bottom section. In one embodiment, this method is carried out wherein the water as the extraction agent is introduced above the feed point. In another embodiment, this method is carried out wherein the amount of introduced water is from 1 to 50 weight percent of the feed load.

The method of the present invention provides several ways of controlling the distillation column in order to achieve the separation of the methanol. A non-limiting example of a distillation control scheme includes, e.g.: (a) setting the reflux to the column to be, for example, a fixed flow rate or a flow rate calculated to be a'fixed multiple of the feed flow rate; (b) applying a thermocouple within the column and the feed point and controlling the reboiler with an automatic controller to obtain the set point temperature at the control thermocouple; and (c) taking samples regularly from the top- and bottom-product, analyzing the acetone, methanol, and water contents of the samples, and, based on the analytical results of the samples, adjusting the reflux controller set point and the control temperature set point to obtain the desired separation of methanol from the acetone. Preferably, the control thermocouple is located in the section of trays or packing below the feed point. Preferably, the automatic controller works by adjusting the heat input to the reboiler by, for example, adjusting the steam flowrate to the reboiler. Optionally, the automatic controller may use pressure compensation of the thermocouple temperature signal. Optionally, the reflux flow rate control strategy may calculated to be a fixed multiple of the feed flow rate, but limited to not exceed a maximum reflux flow rate or fall below a minimum reflux flowrate.

An alternative distillation control scheme includes, e.g.: (a) setting the heat input to the reboiler to be, for example, a fixed steam flow rate or a steam flow rate calculated to be a fixed multiple of the feed flow rate; and (b) applying a thermocouple within the column and controlling the reflux flow rate with an automatic controller to obtain the set point temperature at the control thermocouple. Preferably, the control thermocouple for this alternative scheme is located in the section of trays or packing below the feed point. Optionally, the automatic controller may use pressure compensation of the thermocouple temperature signal. Optionally, the reboiler heat input control strategy may set the steam flow rate to be a fixed multiple of the feed flow rate, but limited to not exceed a maximum steam flow rate or fall below a minimum steam flowrate.

The method of distillation column control is not limited to those examples described above. Methods of controlling distillation columns are well known by those skilled in the art and are extensively described in the literature. For example, methods of controlling distillation columns are described in "Distillation Control: for Productivity and Energy Conservation" by F. Greg Shinskey, McGraw Hill, 1984 and "Practical Distillation Control" by William L. Luyben, Van Nostrand Reinhold, 1992.

The method of the present invention provides a low cost and easy to implement solution for removing methanol from a bisphenol-A production process, thereby preventing deactivation of the mercaptoamine-promoted catalyst. The invention has the advantage that existing distillation columns may be used by easy modification of the operation process of the column, and expensive additional equipment or the disposal of significant amounts or purged raw materials may be avoided. The method of the present invention may also be used for the production of acetone and phenol by the cumene oxidation process.

The present invention also provides a process for the manufacture of bisphenol-A, comprising: (a) reacting phenol and acetone in the presence of a mercaptoamine-modified strong acid cation exchange resin catalyst to produce a reactor effluent containing bisphenol-A; (b) distilling the reactor effluent to remove water, methanol and unreacted acetone; (c) further distilling the water and acetone-rich overheads stream from the first distillation step to recover the unreacted acetone from the water, characterized in that at least 20% of the methanol fed to the second distillation step is leaving with the water stream; and (d) returning at least a portion of the overheads stream from the second distillation step to the reactor as recovered acetone.

The cation exchange resin catalyst used in the reaction step of the process of the present invention may be a cation exchange resin in an acidic form. Preferably, the cation exchange resin used in the present invention has a sulfonic acid group. Examples of the cation exchange resin include sulfonated styrene/divinylbenzene copolymer resins, sulfonated crosslinked styrene resins, phenol-formaldehyde-sulfonic acid resins, and benzene-formaldehyde-sulfonic acid resins.

Examples of commercially available cation exchange resin catalysts useful in the present invention include DOWEX™ 50WX4, DOWEX™ 50WX2, DOWEX™ M-31, DOWEX™ MONOSPHERE M-31, DOWEX™ DR-2030 and DOWEX™ MONOSPHERE DR-2030 catalysts, manufactured and marketed by The Dow Chemical Company.

Other examples of commercially available ion exchange resin catalysts useful in the present invention may include Diaion™ SK104, Diaion™ SK1B, Diaion™ PK208, Diaion™ PK212, and Diaion™ PK216 manufactured by Mitsubishi Chemical Industries, Limited; Amberlyst™-31, Amberlyst™-121, Amberlyst™-232 and Amberlyst™-131 manufactured by Rohm & Haas; T-38, T-66 and T-3825 manufactured by Thermax; Lewatit™ K1131, Lewatit™ K1131S, Lewatit™ K1221, Lewatit™ K1261 and Lewatit™ SC104 manufactured by Lanxess; Indion™ 140, Indion™ 130, Indion™ 180 and Indion™ 225 manufactured by Ion Exchange India Limited; and Purolite™ CT-124, Purolite™ CT-222 and Purolite™ CT-122 manufactured by Purolite.

The mercaptoamine catalyst modifiers used in the reaction step of the process of the present invention are used to improve the selectivity and/or productivity of the catalyst. These modifiers are commonly referred to as "promoters." The modifier may be any promoter of the bound promoter type. Bound promoter means a promoter that contains at least one basic functionality, such as an amino group, that "fixes" the promoter on the catalyst by an acid-base reaction. It is distinguished from the "free" or soluble promoters, which do not have the basic functionality and are usually dissolved in a condensation reaction medium (e.g. a mixture of phenol, acetone, and bisphenol) that is used as a fluid fed into the vessel or reactor during the production of bisphenol A.

Examples of the suitable promoters include an aminoalkanethiol, an alkyl-aminoalkanethiol, a dialkyl-aminoalkanethiol, a thiazolidine, an aromatic mercaptoamine, a mercaptoalkylamide, a pyridinealkanethiol, a mercaptoalkyl phenylpyridine, a N-alkyl-N-mercaptoalkyl-mercaptoalkylaniline, a dimercaptoalkyl pyridine, a mercaptoalkyl-benzylamine, a aminothiophenol, a pyridine alkyl thioester, a pyridine alkyl sulfide, an imidizole alkyl thiol, an imidizole alkyl thioester, an imidizole alkyl sulfide, a phthalimidine alkyl thiol, a phthalimidine alkyl thioester, a polysulfur thioalkyl pyridine, a polysulfur thiopyridine, a polysulfur thio benzothiazole, a polysulfur thio imidizole, a polysulfur thio benzimidizole, or other compound that contains one or more thiol and/or sulfide functionalities and a basic functionality suitable for attachment to a cation exchange resin by an ionic bond. Examples of the one or more thiol and/or sulfide functionalities include functionalities of a R—S—R and a R—SH.

More specifically, examples of aminoalkane thiol include aminoethanethiol, aminopropanethiol, aminobutanethiol, aminopentanethiol, or mixtures thereof.

Examples of pyridine alkane thiol include 4-pyridine methane thiol, 3-pyridine methane thiol, 2-(4-pyridyl) ethane thiol, 2-(2-pyridyl) ethane thiol, 2-(3-pyridyl) ethane thiol, 3-(4-pyridyl) propane thiol, 3-(3-pyridyl) propane thiol, 3-(2-pyridyl) propane thiol, 4-(4-pyridyl) butane thiol, 4-(3-pyridyl) butane thiol, 4-(2-pyridyl) butane thiol, or mixtures thereof.

Examples of thiazolidine include 2,2-dimethylthiazolidine, 2-methyl-2-phenylthiazolidine, 3-methylthiazolidine, 2-methyl-2-ethylthiazolidine, 2,2-(pentamethylene) thiazolidine, 2-methyl-2-dodecylthiazolidine, 2-methyl-2-carbethoxymethylthiazolidine, 2,2,4,5-tetramethylthiazolidine, 2,2,3-trimethylthiazolidine, 2,2-dimethyl-3-octylthiazolidine, 2-methyl-2-ethyl-3-aminoethylthiazolidine, 2-cyclohexylthiazolidine, or mixtures thereof.

Preferably, the promoter may be one of the 2,2'-dimethylthiazolidine, aminoethanethiol, and 2-(4-pyridal) ethane thiol or its isomer.

The promoter is used to modify the catalyst by partially neutralizing the acid groups of the cation exchange resin. Partial neutralization means that a part of the acid groups on the ion exchange resin catalyst are neutralized with the promoter. Preferably, 5% to 50% of the acid groups are neutralized. More preferably, 10% to 30% of the acid groups are neutralized.

The reaction step of the process of the present invention is conducted in a reactor designed to hold a heterogenous catalyst and the reaction fluid, and to allow the reaction fluid to pass over the catalyst. Reactors of this type are well-described in previous literature and well-known to those skilled in the art of bisphenol-A production. One or more reactors may be used, with the reactors arranged in series and/or in parallel.

The reaction step of the process of the present invention is conducted in an excess of phenol to suppress formation of impurities and to limit the temperature increase caused by the heat of reaction. Preferably, a phenol/acetone molar ratio of at least 5:1 is used. More preferably, a molar ratio of phenol to acetone of between 10:1 and 30:1 is used. The feed stream to the reactor may contain bisphenol, bisphenol impurities, and other components. The entire amount of the acetone may be added to the phenol feed stream before the first reactor, or staged addition of the acetone to multiple reactors may be used. The reaction step is preferably conducted at temperatures above the freezing point of phenol and above the crystallization point of the bisphenol-A in the phenol. The reaction step is also preferably conducted at temperatures below which the catalyst degrades or the generation of impurities becomes excessive. Preferably, the reaction temperature is between 40° C. and 115° C. More preferably, the reaction temperature is between 45° C. and 90° C.

The first distillation step of the process of the present invention is done to remove most of the water and the unreacted acetone from the reactor effluent. This distillation step may be done in any distillation equipment, examples of which are known to those skilled in the art of distillation equipment design. Typically, the distillation equipment will comprise a distillation column, a reboiler, and a condenser, and the distillation column will contain either packing or trays and other internal equipment designed to improve the efficiency of the separation. The distillation may be conducted at atmospheric pressure or under vacuum. Preferably, the distillation is conducted under sub-atmospheric pressure to reduce the temperature. This distillation step also removes methanol and other alcohols with the acetone and water, and some phenol and bisphenol may also be codistilled. The overheads stream from this distillation step may comprise acetone, water, phenol, bisphenol, and/or methanol.

In the process of this invention, the reactor effluent may optionally be treated by crystallization and solid/liquid separation to remove a portion of the bisphenol prior to the distillation step where water and unreacted acetone are removed. In this aspect of the process of this invention, the reactor effluent may be: (e) subjected to a crystallization step to precipitate bisphenol/phenol adduct crystals, and (f) the solid/liquid mixture from the crystallization step is then subjected to a solid/liquid separation step to remove the adduct crystals before the crystal-free liquid from the solid/liquid separation step is distilled as described to remove water and unreacted acetone. The crystallization step may be conducted in any crystallizer design, examples of which are known to those skilled in the art of crystallizer design, including draft-tube crystallizers and forced-circulation crystallizers. Heat removal from the crystallizer may be accomplished by direct heat exchange with a coolant, evaporation of a volatile component, or other means. The solid/liquid separation may be conducted in any equipment known to those skilled in the art of solid/liquid separation, including for example centrifuges, pressure filters, vacuum filters, and belt filters.

The following examples are illustrative of the present invention, and are not to be construed as limiting the scope of the invention. Variations and equivalents of these examples will be apparent to those of skill in the art in light of the present disclosure, the drawings, and the claims herein. Unless otherwise stated, all percentages are by weight of the total composition.

EXAMPLES

The following non-limiting examples illustrate the present invention:

Example 1

A commercial process simulator was used to investigate the behavior of a distillation column for the separation of acetone, methanol, and water. An activity-coefficient binary parameter set was derived from readily available vapor-liquid equilibrium data for acetone, methanol, and water. The predicted performance of an atmospheric distillation column for methanol removal is summarized in the drawing, where the fraction of the feed methanol in the bottom product is shown as a function of the acetone content in the column bottom product and the number of theoretical trays in the column. This FIGURE demonstrates that columns with a larger number of theoretical trays will be more effective in rejecting the methanol from the acetone. This FIGURE also demonstrates that higher methanol rejection can be obtained if a larger amount of residual acetone can be tolerated in the column bottoms product.

Example 2

An existing distillation column had been used for many years for the recovery of unreacted acetone from water and other minor components, including phenol and bisphenol A. This column, containing dumped packing, was operated at atmospheric pressure. Recovered acetone was removed from the top of the column, and water and other less volatile impurities were removed from the bottom of the column. The column was typically operated to ensure that less than 10 ppm of acetone remained in the bottoms product. The recovered acetone was combined with makeup acetone and recycled to the reactors. The makeup acetone contained 100-200 ppm methanol. Sampling and analysis of the feed, overheads, bottoms and combined recovered acetone revealed that methanol had accumulated in the process, resulting in as much as 2% methanol (by weight) in the recovered acetone. Removal of methanol from the process without significant capital investment was desired.

The existing column was characterized as having approximately 11 theoretical trays. The process was able to tolerate 100 ppm acetone in the column bottoms, and autoextractive distillation was implemented by using a thermocouple in the bottom section of the tower as the control thermocouple. Adjusting this temperature to maintain 50-100 ppm acetone in the bottoms product allowed a significant fraction of the methanol to be rejected from recovered acetone. Even though less than 50% of the methanol fed to the column left with the column bottoms, this change substantially eliminated the accumulation of methanol due to recycle of the acetone. This solution required no capital investment since modification of the column was unnecessary. Steam usage was reduced, and the cost of the unrecovered acetone was insignificant. This solution was judged to be fully satisfactory.

Although the present invention has been described in considerable detail with regard to certain versions thereof, other versions are possible, and alterations, permutations, and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. A method of separating methanol from acetone recycle streams during production of bisphenol-A, comprising:
    (a) introducing a product stream, including acetone, methanol, water and other components produced during a bisphenol process, as a feed at a feed point into an acetone recovery distillation column comprising a reboiler, a condenser, a bottom section, and a top section;
    (b) condensing a vapor from the top section of the acetone recovery distillation column and returning at least a portion of the condensed vapor to the acetone recovery distillation column as a reflux; and
    (c) setting a flow rate of the feed and a flow rate of the reflux and a heat input to the reboiler such that a bottoms product from the bottom section of the acetone recovery distillation column contains less than 10,000 ppm acetone; wherein at least 20% of the methanol of the feed to the acetone recovery distillation column is leaving with the bottoms product from the bottom section of the acetone recovery distillation column.

2. A method of separating methanol from acetone recycle streams during production of bisphenol-A, comprising:
    (a) introducing a product stream, including acetone, methanol, water, and other components produced during a bisphenol process, as a feed at a feed point into an acetone recovery distillation column comprising a reboiler, a condenser, a top section, and a bottom section;
    (b) introducing water as an extraction agent into the acetone recovery distillation column; and
    (c) condensing a vapor from the top section of the acetone recovery distillation column and returning at least a portion of the condensed vapor to the acetone recovery distillation column as a reflux; and
    (d) setting a flow rate of the feed, a flow rate of the reflux, a flow rate of the introduced water, and a heat input to the reboiler such the bottom section of the acetone recovery distillation column provides a bottoms product having less than 10,000 ppm acetone, and wherein at least 20% of the methanol leaves with the bottoms product from the bottom section of the acetone recovery distillation column.

3. The method according to claim 1, wherein the acetone recovery distillation column comprises at least 6 trays or packing equivalent to at least 6 trays.

4. The method according to claim 1, wherein the acetone recovery distillation column comprises from 10 to 50 trays or packing equivalent to 10 to 50 trays.

5. The method according to claim 1, wherein the acetone recovery distillation column comprises at least 50 trays or packing equivalent to at least 50 trays.

6. The method according to claim 1, comprising operating the acetone recovery distillation column at a pressure of 51 kPa to 203 kPa.

7. The method according to claim 1, comprising operating the acetone recovery distillation column at atmospheric pressure.

8. The method according to claim 1, comprising setting the reflux to be a fixed flow rate or a flow rate calculated to be a fixed multiple of the feed flow rate.

9. The method according to claim 1, comprising setting a flow rate of the feed, and a flow rate of the reflux, and a heat input to the reboiler such that at least 40% of the methanol is leaving with the bottom product.

10. The method according to claim 1, wherein the acetone recovery distillation column further comprises a thermocouple in the bottom section, which acts as a control thermocouple.

11. The method according to claim 1, further comprising controlling a temperature in the bottom section to maintain an acetone concentration of less than 10,000 ppm in the bottoms product.

12. The method according to claim 1, comprising controlling a temperature in the bottom section to maintain an acetone concentration of less than 1000 ppm in the bottoms product.

13. The method according to claim 2, wherein the water as the extraction agent is introduced above the feed point.

14. The method according to claim 2, wherein the introducing includes providing the water at a feed rate such that the introduced water is from 1 to 50 percent of the feed.

15. A process for producing bisphenol-A comprising:
(i) reacting phenol with acetone in the presence of at least one mercaptoamine-promoted sulfonated crosslinked polystyrene cation exchange resin to form a reaction product;
(ii) distilling the reaction product of step (a) to remove acetone, methanol, and water;
(iii) subjecting the acetone, methanol, water, and other components of step (ii) as a product stream to the separation method of claim 1; and
(iv) returning at least a portion of the condensed vapor from the top section of the acetone recovery distillation column to the reaction of step (i) as recovered acetone.

16. A process for producing bisphenol-A comprising:
(i) reacting phenol with acetone in the presence of at least one mercaptoamine-promoted sulfonated crosslinked polystyrene cation exchange resin to form a reaction product;
(ii) subjecting the reaction product of step (i) to a crystallization step to obtain bisphenol/phenol adduct crystals in a mother liquor;
(iii) separating the adduct crystals of step (ii) from the mother liquor;
(iv) distilling the mother liquor to remove acetone, methanol, and water;
(v) subjecting the acetone, methanol, water, and other components of step (iv) as a product stream to the separation method of claim 1; and
(vi) returning at least a portion of the condensed vapor from the top section of the distillation column to the reaction of step (i) as recovered acetone.

* * * * *